United States Patent [19]
Herr et al.

[11] Patent Number: 5,830,472
[45] Date of Patent: Nov. 3, 1998

[54] PURIFIED SPERM SURFACE ANTIGEN, MONOCLONAL ANTIBODY THEREFOR AND APPLICATIONS THEREFOR

[75] Inventors: John C. Herr; Alan B. Diekman; Elizabeth Norton, all of Charlottesville; Ann Westbrook-Case, Gum Spring, all of Va.

[73] Assignee: The University of Virginia Patent Foundation, Charlottesville, Va.

[21] Appl. No.: 671,622

[22] Filed: Jun. 28, 1996

[51] Int. Cl.⁶ .......................... A61K 39/395; C07K 16/00
[52] U.S. Cl. ...................................... 424/152.1; 530/388.2
[58] Field of Search .............................. 530/387.1, 388.2; 424/130.1, 152.1, 178.1

[56] References Cited

U.S. PATENT DOCUMENTS 5,227,160  7/1993  Nudelman et al. .
5,605,803  2/1997  Herr et al. .............................. 435/7.21

OTHER PUBLICATIONS

Mahoney et al. (1991) J. Reprod. Immunol. 19:269–285.

Cone et al. (1994) Am. J. Reprod. Immunol. 32:114–131.

*Primary Examiner*—Frank C. Eisenschenk
*Assistant Examiner*—Patrick Nolan
*Attorney, Agent, or Firm*—Oblon, Spivak, McClelland, Maier & Neustadt, P.C.

[57] ABSTRACT

The monoclonal antibody S19, expressed by Deposit HB12144, ATCC, effectively agglutinates a sperm surface glycoprotein, SAGA-1 protein. The mAB finds utility as a binding agent in a spermicide, showing a high degree of effectiveness in binding potential sperm. The protein bound, identified as SAGA-1, is the immunogen in a contraceptive vaccine, as well as the standard for determining antibody titer upon vaccination. The monoclonal antibody can also be used as a diagnostic to determine the presence, and amount, of sperm in a variety of samples.

5 Claims, 5 Drawing Sheets

```
1           10          20          30          40          50          60
GACATTGTGC  TGACCCAATC  TCCAGCTTCT  CCCTGCCTGT  CAGTCTTGGA  GATCCAGCCT 70          80 CDR-1    90          100         110         120
CCATCTCTTG  CAGATCTAGT  CAGAGTCTTG  TACGCAGAAA  TAGAGACACC  TATTTACATT 130         140         150         160 CDR-2   170         180
GGTTCCTGCA  GAAGCCAGGC  CAGTCTCCAG  AGCTCCTGAT  CTACAGAGTT  TCCAACCGAT 190         200         210         220         230         240
TTTCTGGGGT  CCCAGACAGG  TTCAGTGGCA  GTGGATCAGG  GACAGATTTC  ACACTCAAGA 250         260         270         280 CDR-3   290         300
TCAGCAGAGT  GGAGGCTGAG  GATCTGGGAG  TTTATTTCTG  TTCTCAAAGT  ACACATGTTC 310         320         330         340         350         360
CATTCACGTT  CGGCTCGGGG  ACAAAGTTGG  AAATAAAACG  GGCTGATGCT  GCACCAACTG

368
TATCCATC
```

```
  1 GGGAATTCAT GGAATGGAGC TGGGTTTTCC TCTTCTTGGT AGCAACAGCC
 51 TCAGGTGTCC ACTCCCAGGT CCAATTGCAG CAACCTGGGT CTGAACCGGT
101 GAGGCCTGGA GCTTCAGTGA AGGTGTCCTG CAGGGCTTCT GGCTACAAAT
151 TCACCACCTA CTGGATGCAC TGGGTGAGGC AGAGGCCTGG ACAAGGCCCT
201 GAGTGGATTG GAGATATTTA TCCTGGTAGT GGTGATTCTA ACTACGATGT
251 GAAGTTCAAG AACAAGGCCA CACTGACTGT AGACACATCC TCCAGCACAG
301 TTTACATACA ACTCAGCAGC CTGACATCTG AGGACTCCGC GGTCTATTAC
351 TGTGCAAGAA GGGACTATGG TTGCCCTTTT GTTTACTGGG GCCAAGGGAC
401 TCTGGTCACT GTCTCTGCAG CCAAAACGAC ACCCCCATCC GTTTATCCCC
451 TGGCCCCTAG AACTTGGG
```

FIG.5

PURIFIED SPERM SURFACE ANTIGEN, MONOCLONAL ANTIBODY THEREFOR AND APPLICATIONS THEREFOR

FIELD OF THE INVENTION

This invention pertains to a sperm surface antigen, a monoclonal antibody therefor, and applications for both the monoclonal antibody and the antigen. Specifically, a contraceptive vaccine is provided employing the antigen as an immunogen, as well as a standard for immunity assays, and the monoclonal antibody finds application as a spermicide and diagnostic reagent.

BACKGROUND OF RELATED WORK

Substantially continuous attention is focused on the development of improved contraceptive methods. One widely exploited technology is the use of spermicides, essentially a chemical barrier that prevents penetration of sperm to the uterus or egg, or inhibits the activity thereof, thereby precluding fertilization. One of the most widely used spermicides is a detergent, Nonoxynol-9. Reports indicate an increased incidence of urogenital infections and cervicovaginal inflammation in women employing this detergent spermicide. McGroarty et al, *Journal of Urology*, 152(3):831–833 (1994). As an alternative to chemical detergents, authors have suggested the use of monoclonal antibodies as likely safe active agents for topical applications, such as use in topical spermicides. See, e.g., Cone et al, *Am. J. Reprod. Immunol.*, 32:114–131 (1994). Studies conclude that in addition to the reduction or elimination of unwanted immune reactions, human monoclonal antibodies should present safe spermicides since their dose and duration of application can be readily controlled, topical delivery minimizes systemic exposure and the monoclonal antibody can be selected for safety and efficacy. Therefore, a sperm-active monoclonal antibody delivered as a topical spermicide may produce desired anti-fertility effects without the negative side effects accompanied by detergent spermicides. See generally, Alexander, *Scientific American*, September:136–141 (1995). Accordingly, a goal in the art continues to be the provision of a safe and effective spermicide employing monoclonal antibodies.

A wide variety of monoclonal antibodies have been studied as potential sperm-reacting agents. Among those studied is the anti-human sperm monoclonal antibody S19. The development of this monoclonal antibody is reflected in Anderson et al, *J. Reprod. Immunol.*, 10:231–257 (1987). This antibody was obtained by immunization of mice with human sperm homogenates. The $I_gG_I$ monoclonal antibody was found to strongly agglutinate human sperm in the laboratory of the inventors, and subsequently submitted for further characterization to the World Health Organization-Sponsored Workshops on Anti-Sperm Monoclonal Antibodies. The anti-human sperm monoclonal antibody S19 strongly agglutinates human sperm, inhibits tight binding between human sperm and the zona pellucida and blocks sperm penetration of cervical mucus. Anderson, supra, Cone, supra, Mahoney et al, *J. Reprod. Immunol.*, 19:269–285 (1991). The strong agglutination of sperm by this antibody has been demonstrated visually on videotape. These findings indicate that the cognate S19 antigen is involved in gamete interactions during fertilization, may serve as a target for autoantibodies that contribute to immunologic infertility, and may be a candidate for development as a contraceptive vaccine.

However, the S19 antibody has not been further developed, either as a research tool, or as a contraceptive reagent. No deposit of the S19 antibody has been made, nor has it been "humanized" to reduce the possibility of immunologic reaction. No detailed studies have been carried out on the monoclonal antibody, and to date, it remains essentially a scientific curiosity.

Other monoclonal antibodies and sperm antigens are known. The monoclonal antibody MHS-10 and the antigen which is bound thereby, SP-10, an intraacrosomal antigen, which is a candidate for use both in sperm diagnostics, and as a contraceptive vaccine, is discussed in U.S. Pat. No. 5,436,137, Herr et al, incorporated herein by reference. Unlike the SP-10 antigen, however, the antigen bound by the S19 monoclonal antibody, sperm agglutination antigen-1 (SAGA-1) appears to be localized on the entire surface of human sperm. This strongly suggests that the monoclonal antibody will bind and agglutinate at multiple sites over the entire sperm surface.

Developmental work on vaccines employing the SP-10 antigen are continuing. Similarly, many investigators around the world are looking at the possibility of the development of contraceptive vaccines based on sperm antigens. See, e.g., Aitken et al, *British Medical Journal*, 49:88–99 (1993), Freemerman et al, *Biol. Reprod.*, 50:615–621 (1994) and Herr, *Fertility Control*, pp. 431–452 (Second Edition 1994). In this connection, work continues on human chorionic gonadotropin (hCG) as a contraceptive vaccine for women. Talwar, *Current Opinion in Immunology*, 6:698–704 (1994) and European Patent 86304274.3. While clinical vaccine trials are underway with this potential vaccine, the hCG immunogen employed functions as an abortifactant, that is, immune responses induced by inoculation with this vaccine induce abortion of the early embryo or fetus. This may constitute an unacceptable form of contraceptive for many individuals.

As an alternative, a variety of sperm surface antigens have been employed in studies involving primate and rodent models. Thus, decreased fertility rates resulted from the immunization of test animals with sperm surface antigens such as LDH-C4, O'Hern et al, *Biol. Reprod.*, 52:331–339 (1995), PH-20, Primakoff et al, *Nature*, 335:543,546 (1988), RSA-1, O'Rand et al, *J. Reprod. Immunol.*, 25:89–102 (1993) and fertilin, Ramarao et al, *Mol. Reprod. Dev.*, 43:70–75 (1995). Disappointingly, in primates, the highest rate of efficacy observed with a sperm antigen is about 75 percent inhibition of fertility, O'Hern et al, supra. Thus to date there has not been identified a human sperm antigen that functions as a contraceptive vaccine with a level of efficacy comparable to that of oral contraception. Thus, it remains an object of those of skill in the art to provide a safe and effective contraceptive vaccine with a high rate of fertility inhibition, on the order of the level of efficacy given by oral contraceptives.

Additionally, because those receiving a contraceptive vaccine will require periodic monitoring of serum antibody to determine if they are "safe", use of the SAGA-1 antigen as a target in assays to measure antibody concentration in persons receiving the vaccine is desirable.

"Over the counter" assay or diagnostic kits for the detection of hormones associated with pregnancy (hCG and others) have achieved wide-spread success in the marketplace, as an alternative or a first-step to potentially embarrassing, inconvenient and expensive visits to medical offices. In recent years, attention has been focused on assays for the presence, and concentration of sperm in a users ejaculate. Both from the point of view of fertility counseling, as well as clinical diagnosis in the case of rape, or for the purposes of assaying for the presence and effectiveness of a vasectomy, a convenient test kit, that could be safely and reliably employed at home, for the detection of sperm in a sample, has become increasingly desirable. Such a test kit, employing the MHS-10 monoclonal antibody for the SP-10 intraacrosomal sperm antigen is disclosed in U.S. patent application Ser. No. 08/231,675, which is incorporated herein by reference. The S19 antibody offers an effective binding alternative to the MHS-10 antibody for use in human sperm diagnostics.

SUMMARY OF THE INVENTION

The above goals are met through the use of a "humanized" recombinant version of the monoclonal S19 antibody, and purification and utilization of the corresponding antigen bound thereby, SAGA-1, as active agents. The monoclonal antibody, mobilized through an appropriate vehicle, provides an effective binding agent as a spermicide and as a human sperm diagnostic. The SAGA-1 antigen, a human sperm glycoprotein distributed over the entire surface of the sperm, provides an effective immunogen, as well as a standard for assaying the generation of contraceptive antibodies in those undergoing vaccine therapy.

To provide an effective spermicide gel or cream, the monoclonal antibody must be provided in an effective vehicle. Among other vehicles available for study are non-phospholipid liposomes specifically formulated for antigen or antibody delivery. One commercial embodiment is currently available from Novavax, Inc. of Rockville, Md. under the mark NOVASOMES®. S19 monoclonal antibodies may be bound the surface of these positively-charged liposomes. Other sperm-agglutination vehicles and compositions may be prepared.

Purification of the SAGA-1 antigen is the first step in preparation of an effective vaccine. The purified antigen, incorporated in a pharmaceutically acceptable carrier, can be administered to patients desiring vaccination for contraception. Repeated vaccination results in the generation of antibodies against sperm, highly effective in the binding of sperm. To monitor the development of an effective level of antibodies, the purified antigen may be used as a test standard reagent, to determine the presence and amount of antibodies present in the patient, through conventional diagnostics.

DETAILED DESCRIPTION OF THE INVENTION

Applicant's invention herein encompasses the monoclonal antibody S19, the antigen which it binds, SAGA-1, a spermicide employing the monoclonal antibody in an appropriate pharmaceutically acceptable vehicle, a contraceptive vaccine employing SAGA-1 as the immunogen, and diagnostic assays and kits, employing bound S19 as a diagnostic to determine the concentration of sperm and SAGA-1 as a standard reagent to determine the development of antibodies in response to vaccination therewith, and related applications. Each of these is considered below.

While the antibody, the protein and their applications are considered separately, the invention springs from the common recognition that the SAGA-1 protein is widely distributed over the surface of the sperm, and is positively bound by the S19 monoclonal antibody, which apparently blocks sperm function at multiple steps in the process of fertilization, including inhibition of sperm motility and gamete interactions.

Monoclonal Antibody S19

As noted above, although nowhere previously publicly available, the S19 monoclonal antibody has been the subject of research and prior publication. The original S19 antibody was obtained by the immunization of mice with human sperm homogenates. This anti-human sperm monoclonal antibody strongly agglutinates human sperm, inhibits tight binding between human sperm and zona pellucida, blocks sperm penetration of cervical mucus and induces sperm shaking phenomenon.

The S19 monoclonal antibody has been deposited, under Budapest Treaty conditions, at the ATCC, on Jun. 26, 1996, Deposit No. HB12144. To the best of Applicant's knowledge, this is the first time such a deposit has been made.

The ability of the S19 monoclonal antibody to strongly agglutinate human sperm has been demonstrated, in vitro. The agglutination was analyzed by video microscopy. A video movie has been made.

Demonstration of Agglutination

For each experiment, human semen was diluted to a final concentration of 20 million sperm/ml and ascites was diluted 1:10. Sperm and ascites were mixed in an Eppendorf tube and then placed on a hemacytometer. Results with S19 ascites were noted with time lapse photography. Results with null ascites were noted in real time.

At Time O sperm are free swimming. After 10 minutes sperm are completely agglutinated. As a control, null ascites fluid was employed. (Time O refers to the placement of the sperm on the slide and the start of photograph.) Sperm are free swimming. Debris and round cells are evident. No changes in motility or in degree of agglutination are evident in the control after 10 minutes.

These results indicate that the S19 monoclonal antibody bind and agglutinate human sperm at multiple sites over the entire sperm surface. The complete agglutination of all sperm indicates that anti-SAGA-1 mAB will act as an effective deterrent to sperm function and therefore to fertilization.

Spermicide Preparation

As noted, the literature theorizes the development of a variety of monoclonal antibody-based spermicides. Suitable vehicles are described in Cone and Alexander, supra. Applicants have developed a particular vehicle for the presentation of mAB S19 in agglutinating form, by using the commercially available liposome delivery system available from Novavax, Inc. of Rockville, Md., commercially available under the name Novasomes®. These liposomes are specifically formulated for antigen or antibody delivery. Novasomes® containing native S19 monoclonal antibody molecules bound to the surface of these non-phospholipid positively charged liposomes function effectively as a spermicide in a spermicide gel. The Novasome® formulation was tested using the sperm agglutination assay described. At a 1:10 dilution the S19-Novasome® vehicle agglutinated sperm at the same efficiency as a 1:20 dilution of the S19 ascites fluid. These results indicate that the S19 monoclonal antibody has the same effect on sperm function when incorporated into commercially available delivery systems, as in native fluid.

Alternative delivery systems are available to those of skill in the art. Prominent among these are lipid-conjugated peptides, see e.g., Deres et al, Nature, 342:561–564 (1989) and ISCOMs, see e.g., Takahashi, Nature, 344:873–875 (1990). Other preparations, including hydrophobic emulsions and saponins, have been developed. in the past for the processing and presentation of specific peptides, and may be used in connection with the antibodies of the spermicide addressed herein. See, e.g., Raychaudhuri et al, Proceedings of the National Academy of Science, U.S.A. 89:8308–8312 (1992) and Newman et al, J. Immunol. 148:2357–2362 (1992). Other vehicles, including the presentation of the antibodies on a membrane, such as that expressed by recombinant virus (i.e., recombinant viral schemes wherein the DNA encoding the antibody, see, infra, is expressed in an recombinant cell together with a structural membrane protein) may be used. Of the available varieties, in addition to the non-phospholipid liposomes described above, ISCOMs, commonly used in vaccines for the presentation of antigens, offer desirable features. ISCOMs form cage-like membrane structures into which or on which the antibody can be presented. ISCOMs have previously been used in connection with the presentation of antigens, but they similarly present antibody proteins in an exposed, virus-like structure. In this respect, other vehicles known for the presentation of active proteins, including co-polymer spheres, and virus-like particles (VLPs) have been known to achieve results similar to the immune-stimulating complexes, or ISCOMs. Of course, a system conventional in the extreme, the attachment of the antibody, via coupling agent, to the surface of a microsphere, may be suitably used in conjunction with acceptable manufacturing techniques for the formulation of gels and creams consistent with this approach.

Thus, the essence of Applicant's spermicide is the incorporation, in a suitable carrier, of a sufficient concentration of S19 mAB in an appropriate vehicle to effectively inhibit (agglutinate or bind) all sperm present in an ejaculate.

Isolation, Characterization and Cloning of the S19 mAB

MHS-8 hybridoma cells secreting S19 were grown and counted such that 10 million cells were processed for RNA collection utilizing the FastTrack 2.0 kit (Invitrogen). Total RNA was directly isolated from the cells using a detergent lysis and protein degradation buffer. Poly(A)+RNA was then isolated using a modified Aviv and Leder protocol in which the mRNA is bound to oligo dT resin. The resin was then washed with a low salt buffer to remove extraneous total RNA, and the poly(A)+RNA was eluted from the resin. Spectrophotometric analysis at 260 nm and 280 nm revealed a final concentration of 1.84 µg/µl poly(A)+RNA.

Reverse Transcription and Amplification of Poly(A) +RNA

S19, a bivalent antibody, functions as a human sperm agglutinin through its ability to cross-link epitopes on the sperm surface. To preserve this function in a recombinant protein, the epitope-recognizing regions or complimentary determining regions (CDRs) of the antibody were identified. Four murine oligonucleotides were made for the $I_gG_1$-specific heavy chain and light (kappa) chain subunits. The oligos were designed such that they would amplify only the variable regions (approximately the first 360 base pairs) of S19, which contain the CDRs. They were as follows:

1. Heavy chain 5' end: (SEQ ID NO:3)  ACTAGTCGACATGAGAGTGCTGATTCTTTTGTG

2. Heavy chain 3' end: (SEQ ID NO:4)  CCCAAGCTTCCAGGGRCCARKGGATARACI GRTGG

3. Light chain 5' end: (SEQ ID NO:5)  CCCCCCGGGGACATTGTGCTGACCCAATCTCCAGCTTCT

4. Light chain 3' end: (SEQ ID NO:6)  CCCCCCGGGGATGGATACAGTTGGTGCAGCATCAGCCCG

Heavy chain oligos were obtained from the Ig-Prime kit (Novagen), and the nucleotide abbreviations are as follows: R=A or G, I=inosine, and K=G or T. All oligonucleotides were diluted to a final concentration of 1.0 µg/µl with dH$_2$O.

Figure 1:
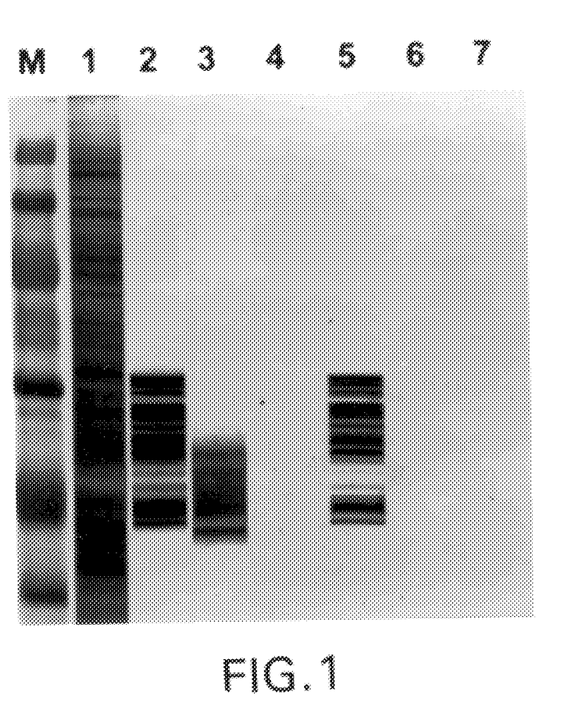
FIG. 1 is a photograph of the results of a Western blot analysis obtained by S19 mAB reaction with SAGA-1.

Reverse transcription and polymerase chain reaction amplification of S19 hybridoma poly(A)+RNA were performed in a single reaction using the Access RT-PCR system from Promega. Briefly, 5 µg of S19 hybridoma poly(A)+ RNA, 1 µg of each appropriate primer (primers 1 and 2 for the heavy chain, primers 3 and 4 for the light chain), 1 µl 10 mM dNTP mix, 10 µl of 5×AMV reverse transcription buffer, 2 µl 25 mM MgSO$_4$, 1 µl AMV reverse transcriptase, 1 µl Tfl polymerase, and 30 µl nuclease-free dH$_2$O were combined in a 0.5 ml microfuge tube. The reaction was incubated at 48° C. for 45 minutes, followed by a 2 minute incubation at 94° C. The reaction was cycled 40 times: 94° C. for 30 seconds, 60° C. for 1 minute, 68° C. for 2 minutes. A 7 minute incubation at 68° C. followed the final cycle. Amplified products were analyzed on a 2% agarose gel (FIG. 1). Lane 1, a 1 kb DNA marker from Stratagene; Lane 2, the light chain fragment, and Lane 3, the heavy chain fragment. The heavy and light chain bands ran approximately at the same mobility as the 396 bp marker as expected, since the primers for the light chain amplify the first 384 bp (the 360 bp with additional restriction enzyme sites), and those for the heavy chain amplify an additional 60 bp.

Cloning of the Amplified S19 Antibody Fragments into a Vector

The heavy and light chain bands from FIG. 1 were cut out of the gel and eluted using Ultrafree MC filter units (Millipore). These purified fragments were subsequently amplified by another 40 cycles or PCR with Pfu polymerase in place of Tfl polymerase. Again, the fragments were gel purified and resuspended in 25 μl of dH₂O.

Cloning was performed using the pCR-Script SK(+) system (Stratagene). This vector uses the blunt-end ligation of Pfu-c amplified PCR fragments to incorporate the cDNA into a SrfI restriction enzyme site in the vector. SrfI is a novel rare-cleavage restriction enzyme that recognizes the sequence 5'GCCCGGGC3'. To ensure that the heavy and light chain fragments would not be digested by SrfI, 1 μl of each CDNA was combined with 1 μl of SrfI enzyme, 1 μl 10×Reaction buffer, and 7 μl dH₂O for 1 hour at 37° C. Neither fragment was digested by the enzyme.

The cloning was then carried out by combining 1 μl pCR-Script vector, 1 μl pCR-Script 10×buffer, 0.5 μl 10 mM rATP, 5.5 μl heavy or light chain cDNA, 1 μl SrfI enzyme, and 1 μl T4 DNA ligase. Reaction tubes were incubated at room temperature for 1 hour, and then heated at 65° C. for 10 minutes.

Epicurean Coli XL1-Blue MRF' Kan supercompetent cells were thawed on ice and 40 μl were aliquoted into pre-chilled 15 ml tubes. 0.7 μl of 1.44M β-mercaptoethanol was then added to the cells which were incubated on ice for 10 minutes. For each of the cloning reactions above, 2 μl were added to the cells and left on ice for an additional 30 minutes. The cells and cDNA mix were then heated in a 42° C. bath for 45 seconds, and transferred to ice for 2 minutes. Following addition of 0.45 ml SOC media, the cells were shaken in a 37° C. water bath for 1 hour. These cells were then spread on LB/ampicillin/methicillin/X-gal/IPTG petri plates to select for antibiotic resistant colonies and incubated overnight at 37° C. Positive colonies of each clone were chosen and grown up in 5 ml SOC cultures for plasmid purification.

Plasmids were purified using Qiagen-tip 20 columns (Qiagen). The 5 ml of cells were centrifuged for 5 minutes at 10k rpm. Excess media was aspirated, and the cell pellet was resuspended in 0.3 ml of buffer P1. Buffer P2 was added, and the mixture was incubated at room temperature for 5 minutes. 0.3 ml of chilled buffer P3 was then added and the mixture was incubated on ice for 10 minutes. During this incubation Qiagen columns were equilibrated by applying 1 ml of QBT buffer. The cell samples were then centrifuged for 15 minutes at 10k rpm and the supernatant removed and loaded onto the Qiagen-tip 20 columns. After the supernatants fully entered the column resin by gravity flow the columns were washed with 4 ml of buffer QC and eluted with 0.8 ml buffer QF. To precipitate the plasmid DNA a volume of 0.56 ml of isopropanol was added to the column eluant and the combination centrifuged at 10k rpm for 30 minutes. The resulting DNA pellet were then resuspended in 25 μl of dH₂O.

To confirm the presence of a cDNA insert in the purified plasmids each clone was digested with two restriction enzymes. The restriction enzymes used for digestion were Not1 and EcoR1 which have restriction sites at the 5' and 3' end, respectively, of the pCR-Script cloning vector. If an insert is present, digestion with these enzymes will excise it from the host vector. 1.5 μl of each clone was combined with 0.75 μl of Not1, 0.75 μl EcoR1, 1.5 μl of 10×buffer, 10.5 μl of dH₂O, and incubated at 37° C. for 90 minutes. The digestions were then run on a 2% agarose gel, and those clones that contained an insert were sequenced.

Sequence Analysis of Heavy and Light Chain Clones

Figure 5:
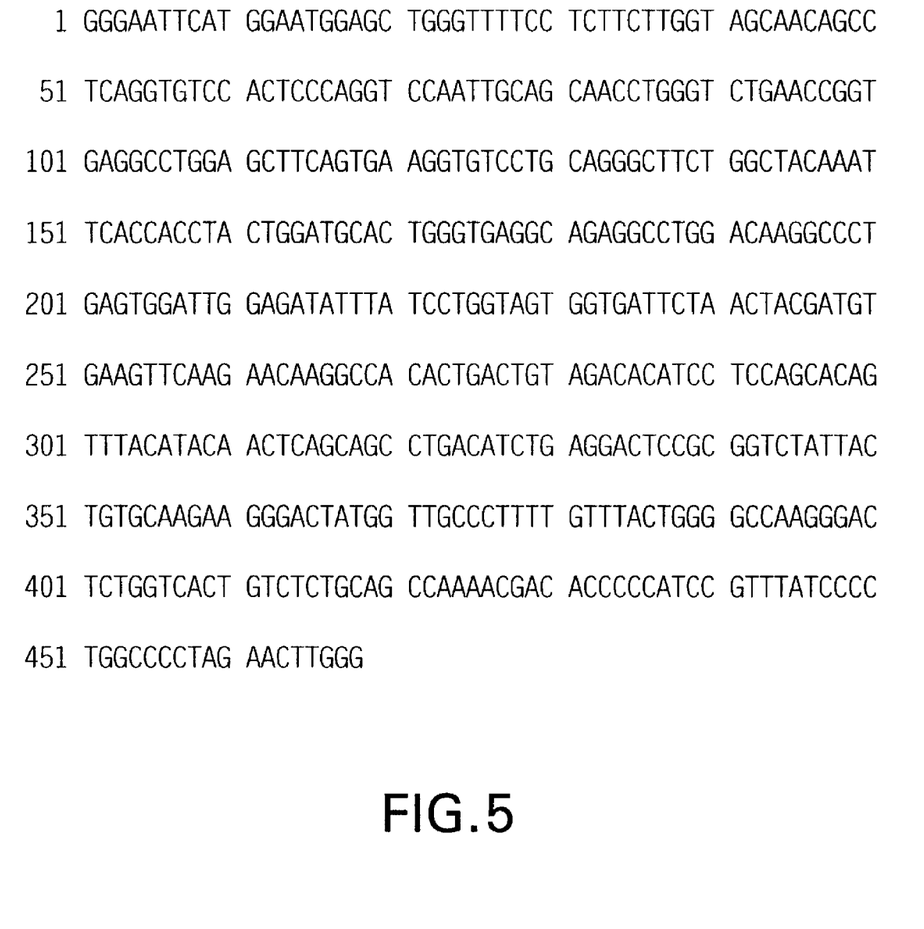
FIG. 5 is the nucleotide base sequence for the heavy chain of the S19 mAB as obtained by sequence analysis (SEQ ID NO:2).

The positive clones from above were sequenced using the Fidelity kit (Oncor). Each sequencing reaction consisted of 5 μl of plasmid DNA, 1 μl T3 primer (which lies upstream of the 5 cloning site on the pCR-Script vector), and 2 μl dH₂O. These were heated to 95° C. for 5 minutes, briefly centrifuged, 2 μl of annealing buffer was added, and the reactions were incubated at 370° C. for 15 minutes. The reactions were then labelled by the addition of 3 μl T4 reaction buffer, 1 μl ³³PαATP, 2 μl T4 DNA polymerase, and 2 μl dH₂O. This mix was incubated at 400° C. for 15 minutes and then 6 μl of T4 accessory mix was added. From this labelling reaction, 5.5 μl was added to each of 4 tubes containing 2 μl of either A, C, G, or T termination mix and incubated at 40° C. for 5 minutes. The reactions were stopped by the addition of 5 μl of Proteinase K solution and heated to 95° C. prior to loading on a 6% acrylamide sequencing gel. The gel was then run for 2 hours at 2000 volts, dried onto Whatman 3 MM filter paper under vacuum, and exposed to x-ray film overnight at room temperature. After development of the film the gels were read on a lightbox. By comparing the deduced clone sequences to known murine I₉G₁ sequences it was found that the light chain clones represented an aberrant light chain amplified from the hybridoma sp2/0. The heavy chain sequence was isolated and the base sequence is reflected in FIG. 5 (SEQ ID NO:2).

Restriction Enzyme Digests of CDNA to Remove Endogenous Antibody

To separate the S19 kappa light chain from the aberrant hybridoma light chain the RT-PCR reactions were repeated. The aberrant sequence was analyzed and found to have a rare Van91I restriction site (5'CCANNNNNTGG3'SEQ ID NO:7) in one of the CDRs. Assuming that the S19 light chain was present in the RT-PCT amplified cDNA mix from the hybridomas, this mixture was digested with Van91I (New England Biolabs). The digestion reaction consisted of 1 μl Van91I, 3 μl cDNA, 1 μl 10×reaction buffer, and 5 μl dH₂O. The reaction was incubated overnight at 37° C. to ensure complete digestion. Any CDNA not cut by the enzyme should be the correct S19 kappa light chain.

Figure 2:
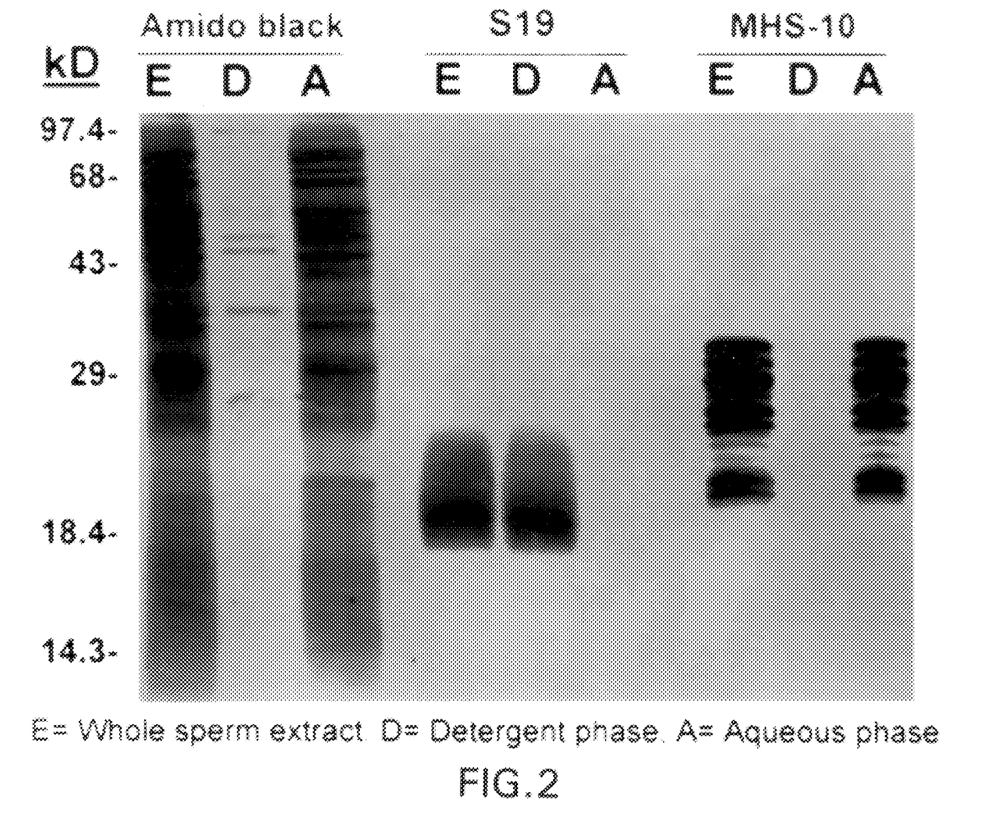
FIG. 2 is a photograph of the results of an SDS-page immunoblot of Triton-X-114 phase partitioning of SAGA-1.

As shown in FIG. 2, the digest was analyzed on a 2% agarose gel. (Lane 1 is the Stratagene 1 kb DNA marker, Lane 2 is 3 μl of uncut cDNA, and Lane 3 is the digested reaction). In Lane 3 the majority of the reaction has been digested into 2 fragments but there is a faint band at 396 bp representing the uncut putative S19 light chain. This band was cut out from the gel and purified as above, then amplified by 40 cycles of PCR with Pfu polymerase as previously described. The DNA was then cloned into the pCR-Script vector as before and six positive colonies were chosen by the same plating method. Again, these positive colonies were grown, plasmid purified and restriction digested to confirm the presence of an insert.

Automated Sequencing of the Kappa Light Chain

Figure 3:
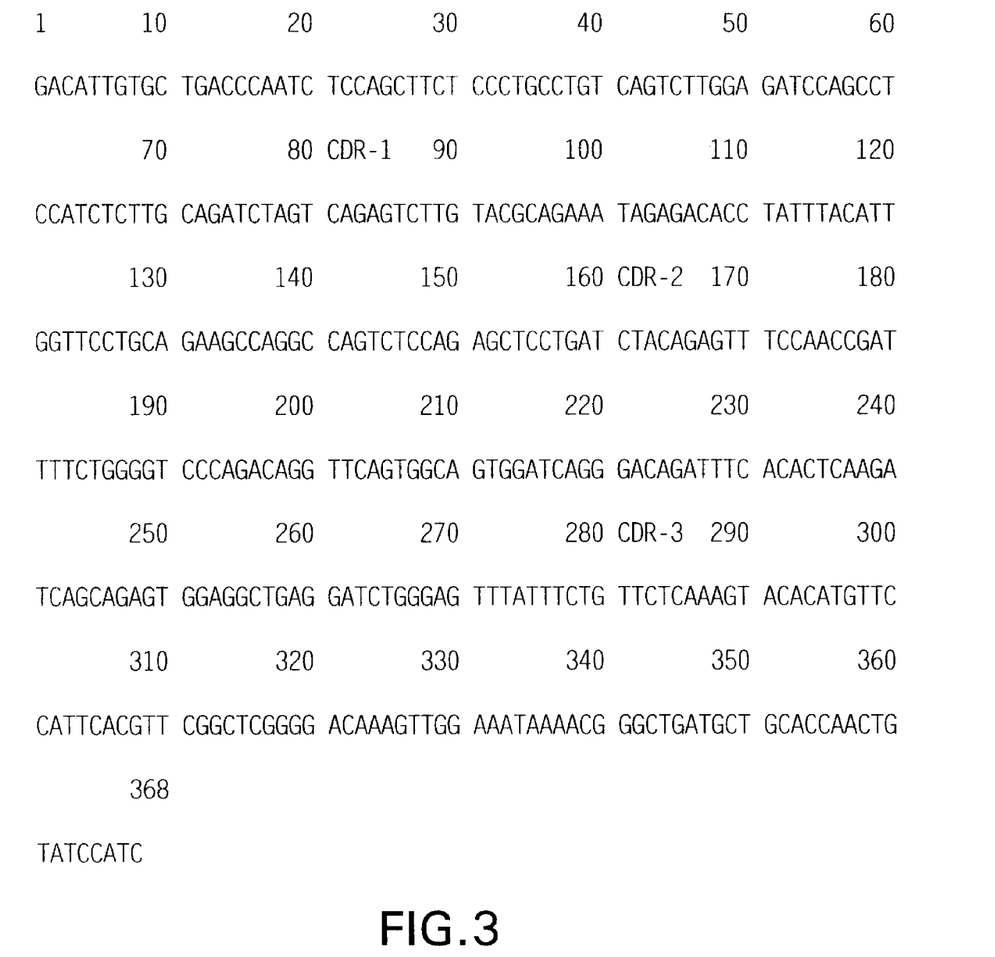
FIG. 3 is the nucleotide base sequence for the Kappa light chain of the S19 mnAB as obtained by sequence analysis (SEQ ID NO:1).

Sequencing of the new light chain clones was performed in the University of Virginia Biomolecular Research Facility using an ABI Prism 377 Automated DNA Sequencer. For each clone, 100 ng of cDNA and 3.2 pmol of T3 primer were combined in a total volume of 12 μl and delivered to the facility. There the four dye-labeled dideoxy nucleotides and AmpliTaq polymerase FS were added in the same reaction tube. The entire reaction was loaded in a single lane for electrophoresis on a 36 cm well-to-read 5.0% acrylamide gel. Real time detection of the electrophoresed individual fragments was achieved with laser scanning with CCD camera imaging production. The sequencing results from the facility closely match murine kappa light chains from the Gen Bank database, and the correct light chain base sequence is shown in FIG. 3. The sequences of cNDA for heavy and light chains of the S19 in AB can be emloyed, using conventional technology, to provide recombinant antibodies, including antibodies with site deletions and domain deletions and additions.

The SAGA-1 Protein

The now-deposited S19 mAB effectively binds and agglutinates human sperm. The results of photographed agglutination assays clearly demonstrate that binding and agglutination occurs at multiple sites over the entire sperm surface. In addition to the effective spermicide provided by S19 MAB, the bound antigen, SAGA-1, is strongly indicated to be an effective vaccinogen. Specifically, the ability to generate antibodies to the SAGA-1 protein as an antigen/immunogen should provide human females with effective protection against fertilization, i.e., a contraceptive vaccine. The same antigen can be used as a standard test reagent for monitoring the effectiveness of a vaccine protocol. Thus, vaccinated women may be assayed, on a periodic basis, and the fluid sample tested against a known quantity of SAGA-1, in conventional assay formats, including ELISA and Western and Southern blotting assays. A positive binding reflects generation of antibodies which bind the SAGA-1 protein, and thus, protection against fertilization. By using the SAGA-1 as a standardized test, and testing for the amount of binding, the titer, or concentration of antibodies generated, can be measured. As adequate titers can be established by relying on the agglutination assay discussed above, an assay using the SAGA-1 protein as a standard reflecting adequate titers is confirmation of achieving an anti-fertility state, which then need only be maintained over the desired period of infertility.

IDENTIFICATION OF THE SAGA-1 PROTEIN

The S19 monoclonal antibody identifies SAGA-1 as a series of low-molecular weight glycoproteins by Western blot analysis (FIG. 1). An extract of washed human sperm was prepared in 1 percent SDS and separated by reducing SDS-PAGE. The S19 monoclonal antibody reacted with a series of overlapping bands that range from approximately 15 to 25 kD (Lane 3). S19 immunoreactivity with the cognate antigen was abolished by treatment with 10 mM periodic acid (Lane 6) while the reactivity of the MHS-10 monoclonal antibody with a peptide epitope of the SP-10 protein was unaffected (Lanes 2 and 5). This finding indicated that the epitope recognized by the S19 monoclonal antibody is a carbohydrate moiety. (FIG. 1; Lane 1, amido black staining, Lanes 2 and 5, MHS-10; Lanes 3 and 6, S19; Lanes 4 and 7, null ascites; Lanes 2–4, no periodic acid treatment,; Lanes 5–7, immunoblot strips treated with periodic acid; M, molecular weight markers in kD: 97.4, 68, 43, 29, 18.4, 14.3). Furthermore, treatment of the SDS sperm extract with proteinase K destroyed S19 immunoreactivity (data not shown) indicating that the S19 antigen is likely a glycoprotein. The identified S19 glycoprotein was designated Sperm Agglutination Antigen-1 (SAGA-1) based on its ability to strongly agglutinate human sperm.

METHOD FOR HIGHLY ENRICHING SAGA-1

The solubility characteristics of SAGA-1 indicate that it is a hydrophobic, integral membrane protein. S19 reactivity was not detected in human sperm extracts prepared with high salt (1M NaCl or 0.6M KCl) and/or mild non-ionic detergent (0.1 percent NP-40 or Triton X-100). These results indicated that SAGA-1 is not extracted with treatments classically used to remove peripheral proteins.

Further evidence that SAGA-1 exists as an integral membrane protein was examined using Triton X-114 phase partitioning as described by Bordier (1981). Non-ionic detergents, such as Triton X-114, solubilize integral membrane proteins by replacing the normal lipid environment. Triton X-114 forms small micelles at 0° C. when dispersed in aqueous solution above its critical micelle concentration. Hydrophobic integral membrane proteins are incorporated into these micelles while hydrophilic proteins remain in the aqueous environment. When such a solution is heated, the micelles increase in size and come out of solution forming a detergent-rich phase that can be separated from the aqueous solution by centrifugation. Bordier (1981) used this method to demonstrate that most integral membrane proteins partition with the detergent phase while hydrophilic proteins remain in the aqueous phase.

To study Triton X-114 phase partitioning of SAGA-1, washed human sperm were extracted in 1 percent Triton X-114, 10 mM Tris-HCl, pH 7.4, 150 mM NaCl at 4° C. and centrifugated to remove debris. Following three cycles of phase partitioning, equivalent amounts of the initial sperm extract, the detergent phase and the aqueous phase were analyzed by SDS-PAGE and immunoblotting (FIG. 2). The human sperm/testis-specific protein SP-10, a peripheral, acrosomal membrane protein served as a control; reactivity of the MHS-10 monoclonal antibody with SP-10 was detected in the aqueous phase. S19 reactivity was detected in the initial sperm extract and in the detergent phase but not in the aqueous phase. These results indicate that the S19 monoclonal antibody reacts with a hydrophobic, integral membrane glycoprotein. Amido black staining showed that the majority of total sperm proteins remained soluble in the aqueous phase while few proteins partitioned with Triton X-114. Therefore, Triton X-114 phase partitioning will be useful as an initial step in the purification of native SAGA-1.

DETERGENT SUBSTITUTION IS REQUIRED FOR PURIFICATION

The biochemical properties of the detergent Triton X-114 were not conducive with subsequent purification methods. At the required concentration of this detergent, Triton X-114 incorporates protein into large detergent micelles that mask protein binding to an affinity matrix. Furthermore, the Triton X-114 cannot be used at room temperature. Therefore, protein in the Triton X-114 extract was precipitated with −20° C. acetone and resuspended in 0.5 percent octyl glucoside, TBS (10 mM Tris-Hcl [pH 7.4], 150 mM NaCl). Octyl glucoside can be used at room temperature and the required concentration does not inhibit protein-immunomatrix interactions.

Figure 4:
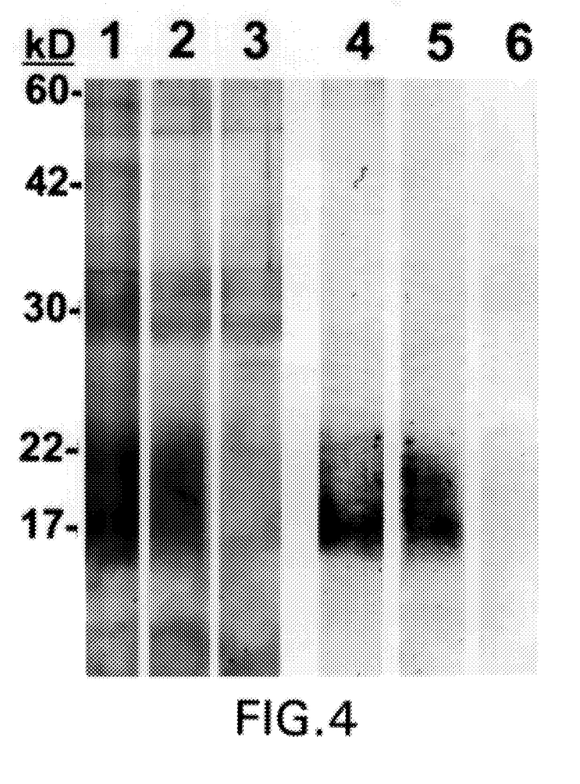
FIG. 4 is a photograph of a Western blotting analysis of a SAGA-1 preparation as bound by a S19 mAB immunomatrix column.

The S19 monoclonal antibody was crosslinked to Protein G-Sepharose with dimethyl pimelimidate dihydrochloride as detailed below. This immunomatrix and Protein G-sepharose beads lacking crosslinked monoclonal antibody, a negative control for antibody specificity, were incubated with the octyl glycoside extract. Bound fractions were subjected to Western analysis with the S19 monoclonal antibody (FIG. 4). SAGA-1 was identified in the octyl glucoside extract and in the fraction that bound the immunomatrix but not in the fraction eluted from the Protein G-Sepharose beads without antibody. These results indicate that SAGA-1 bound specifically to the immunomatrix. The approximately 42 kD bands observed in each lane of the silver stained gel were shown to be contaminants present in the gel loading buffer. (FIG. 3; lanes 1–3, silver stain; Lanes 4–6, Western blot; Lanes 1 and 4, octyl glucoside extract incubated with the immunomatrix: Lanes 2 and 5, protein fraction that bound to the protein -G-S19 immunomatrix; Lanes 3 and 6, protein fraction that bound to the protein-G-Sepharose beads alone).

PROTOCOL FOR THE IMMUNOAFFINITY PURIFICATION OF SAGA-1 FROM HUMAN SPERM

Sperm extract preparation: Allow twenty to thirty human ejaculates to liquefy at room temperature, wash twice by centrifugation at 400×g with Ham's F-10 medium buffered with 0.1M Hepes (pH 7.4) and store frozen until use.

Phase separation: Pool thawed pellets and extract at 4° C. in TBS (10 mM Tris-HCl [pH 7.4], 150 mM NaCl) containing 1.7 percent Triton X-114 and centrifuge at 13,000×g to remove debris. Heat the extract at 30° C. for 3 minutes and centrifuge at 300×g for 3 minutes to separate the detergent and aqueous phases. Repartition each phase twice to ensure complete separation. Clarify the final detergent phase by ultracentrifugation at 100,000×g to remove insoluble debris. Immunoblot analysis with S19 should confirm that SAGA-1 partitioned with the detergent phase.

Acetone precipitation and resuspension in octyl glucoside: To precipitate protein in the Triton X-114 extract, add 8 volumes of −20° C. acetone, mix, and store 4 hours to overnight at −20° C. Collect the precipitate by centrifugation at 3000×g, decant the supernatant, and allow the pellet to air dry. Resuspend the pellet in 0.5 percent octyl glucoside, TBS at twice the original volume of the Triton x-114 extract. Ultracentrifuge at 100,000×g for 1 hour at 4° C. to remove insoluble proteins. Remove supernatant for use in affinity chromatography.

S19 Immunomatrix preparations: Partially purify immunoglobulins from pooled ascites containing S19 by precipitation with 50 percent ammonium sulfate. Wash precipitate twice with 50 percent ammonium sulfate and resuspend in PBS (20 mM NaPO$_4$, 150 mM NaCl, pH 7.4) at one-tenth the original volume of ascites. Dialyze against PBS to remove ammonium sulfate. Determine protein concentration using the BCA Reagent Assay Kit (Pierce Chemical Company). Incubate ammonium sulfate-precipitated protein with Protein G-Sepharose beads (Pharmacia, Piscataway, N.J.) in PBS, pH 7.4 overnight at 4° C. to allow IgG to bind. Include 15 mg of ammonium-sulfate precipitated protein for each ml of Protein G-sepharose beads. Pour the bead slurry into a chromatography column and wash with PBS (pH 8.2) until protein is no longer detected in the eluate as monitored by UV absorbance at $A_{280}$. To covalently crosslink bound IgG to the Protein G beads, equilibrate the column with 0.2M triethanolamine (pH 8.2), resuspend the matrix in 20 volumes of 20 mM dimethyl pimelimidate dihydrochloride, 0.2M triethanolamine (pH 8.2) and incubate for 45 minutes, with gentle agitation at room temperature. To stop the crosslinking reaction, centrifuge the beads (500×g for 3 minutes), resuspend the beads in an equal volume of 20 mM ethanolamine and incubate this suspension for 5 minutes at room temperature. Pour the bead slurry into a chromatography column, equilibrate with 0.2 percent sodium azide, PBS (pH 8.2) and store at 4° C. until use.

Affinity chromatography: Equilibrate the prepared immunoaffinity column with 0.5 percent octyl glucoside, TBS. Recirculate the octyl glucoside solution containing hydrophobic sperm proteins over the column at 1.3 ml/min. continuously for 16 hours at 4° C. Wash the column with 0.5 percent octyl glucoside, TBS to remove unbound material and monitor protein concentration in the wash by UV absorbance. After removal of unbound protein, elute bound material with 0.1M glycine, 0.15M NaCl (pH 2.4), 0.5 percent SDS. Collect 3 ml fractions and monitor their protein concentration with the BCA Reagent Assay kit and UV absorbance. Pool fractions containing protein and concentrate using an Amicon membrane filtration concentrator.

Analysis of sample purity: Separate protein purified on the S19 immunoaffinity column by SDS-PAGE through 15 percent acrylamide and either silver stain or transfer to nitrocellulose. Test immunoblots for reactivity with SAGA-1 by incubation with the S19 monoclonal antibody followed by standard Western blot analysis. Compare the molecular mass and number of protein bands detected by silver staining and by S19 reactivity to estimate purity.

VACCINE

Applicant's invention embraces a contraceptive vaccine employing the SAGA-1 and specifically, any protein which is bound by mAB S19, as an immunogen. SAGA-1 immunization will generate antibodies in the host, sufficient for the purposes of inhibition of fertilization. Preparation of the vaccine itself follows a traditional format. The purified immunogen, preferably a recombinant immunogen having the S19 epitopic regions, is incorporated in a suitable pharmaceutical carrier.

The preparation of an acceptable vaccine, using applicant's novel immunogen, can be obtained following traditional methods. The vaccines described in Aitken, Freemerman and Herr, supra, can be easily adapted to the SAGA-1 protein, and its derivatives bound by the S19 mAB. In particular, contraceptive vaccines employing the PH-20 protein developed by Primakoff, supra and Primakoff et al, and Primakoff, *Am. J. Reprod. Immunol.*, 31:208–210 (1994) reflect a successful adaptation of a sperm protein antigen to a vaccine immunogen in a suitable carrier. While the proteins employed in Primakoff and the others were unfortunately unable to give a high (in excess of 95 percent) degree of fertilization inhibition in primates, the specific character of the SAGA-1 protein, in particular, its thorough distribution over the entire surface of the sperm cell, and the numerous avenues for interaction between it and the monoclonal antibodies responsive thereto, provide an opportunity to achieve fertilization inhibition on the order of oral contraceptives (i.e., 99 percent). To develop adequate antibody titer, it is probable that most test subjects, including female humans, will need to be vaccinated according to a protocol, with widely spaced injections, to give time for the generation of the appropriate antibody titer after each injection. Injections administered about one month apart, followed by an assay using the SAGA-1 protein as a standard for determining antibody titer, should be adequate after a period of about three months, to give sufficient fertilization inhibition for purposes of reliable use. Of course, where the diagnostic assay reflects a lower antibody titer, such that nearly complete fertilization inhibition is not provided, a further vaccination program, or other testing to determine the reason for low antibody titer, should be undertaken.

The use of an immunogen to generate antibodies to the natural state antigen, or a recombinant antigen, both of which are embraced by the claimed invention, is, per se, routine to those of ordinary skill in the art. Applicant's novel development extends to the incorporation and reliance on the unique SAGA-1 protein, first fully characterized herein.

Routine optimization of dosages, vehicles, presentation modes and the like do not constitute an aspect of the invention, per se. Nonetheless, it is suggested, as a routine dosage that a dosage range of 100 μg SAGA-1 protein–500 μg SAGA-1 protein in a volume of 0.5 ml, be suitable as an individual dosage value. Because the antibodies generated by the vaccination program will agglutinate sperm more effectively than other specific anti-sperm antibodies, due to binding over an increased surface area, enhanced effectiveness of the vaccine is obtained.

As is common with most vaccines, a multivalent vaccine is frequently more effective than a single one. As noted previously, numerous sperm-specific antigens, in addition to SAGA-1, are known. Although, individually, these antigens do not give rise to a high degree of confidence of fertilization inhibition, they can be added to a SAGA-1-based vaccine, to give further reliability. In particular, a combination of SAGA-1 and SP-10 is desirable as the immunogen for a multivalent vaccine. Since research demonstrates that antibodies to these proteins are readily developed, the generation of combined binding ability to both proteins, as well as other art-recognized proteins that may be added as immunogenic members of a multivalent vaccine, is possible. It is essential, however, that the SAGA-1 protein, or any variant protein bound by the S19 antibody, be a central element of the vaccine, as the antibodies thereto provide greatly enhanced binding opportunities, and therefore, a greater degree of confidence of fertilization inhibition.

DIAGNOSTIC

The properties of proteins bound by the S19 mAB, including the SAGA-1 protein, make two different types of diagnostic testing possible. Initially, it is necessary to monitor the development of antibodies to the vaccine immunogen, the SAGA-1 protein or variants thereof. Certain potential candidates may lack a suitable immune response system, and many individuals vary in the antibody titer generated in response to any immunogen, or protocol of immunogen administration. Development of an adequate antibody titer may be easily confirmed using the SAGA-1 protein as an antigen standard. Using the agglutination assay described above with respect to the S19 mAB, one can easily determine the concentration necessary for 100 percent agglutination. This concentration of SAGA-1 protein, properly immobilized and presented, is tested against a sample drawn from the patient. Achievement of 100 percent binding suggests an adequate antibody titer. Because any such vaccination program must be conducted under clinical supervision, the testing format may be conventional, using ELISA, Western blotting analysis or other established art formats.

There is, in addition, increasing interest in simple-to-use, "user friendly" commercial diagnostics, that is, over the counter diagnostics. The reasons for interests in this type of diagnostic, and the variety of uses for such a diagnostic, are discussed in detail in U.S. patent application Ser. No. 08/231,675, which is incorporated herein by reference. The diagnostics disclosed therein employ the SP-10 binding antibody, MHS-10, or antibodies having the binding characteristics of those expressed by a hybridoma cell line at the ATCC available under Accession No. HB 10039. As described in the incorporated application, this type of over the counter diagnostic finds application in forensic environments, can be useful in determining the presence of normal germ cell lineage, finds substantial value in those experiencing difficulty in achieving conception, in vasectomized males and the testing of vasectomized males, both by males and females, as well as the testing of vasovasostomized males, to determine the success of surgical reconnection. For any of a variety of reasons, determination of the presence of sperm in a biological sample, either an ejaculate or a sample derived from an ejaculate or from the male reproductive tract, is of significant medical importance. The antigen bound by the S19 mAB, the SAGA-1 protein and corresponding variants and recombinant derivatives, having the S19 CDR-responsive epitope, can be employed in assay formats such as those described in the incorporated pending U.S. patent application Ser. No. 08/231,675.

Thus, the S19 antibody may be bound to a solid phase and used to capture the SAGA-1 protein. Recognition of the presence of the SAGA-1 antigen may be completed by use of a second monoclonal or polyclonal reagent. See, e.g., Shen et al, *Am. J. Reprod. Immunol.*, 29:231–240 (1993). Other assay formats could utilize a wick or dipstick, and antibody coded colored beads. In all these variations, the essential reagent is the S19 MAB, or similar antibody to the SAGA-1 protein. Any protein present in the sample tested is bound or captured by the immobilized antibody. Thus, in the diagnostic intended to monitor development of adequate antibody titer, the SAGA-1 protein or similar protein is used as the standard test reagent. In the "home test kit", wherein verification of the presence of the antigen is desired, thereby verifying the presence of sperm, the monoclonal antibody responsive thereto is the reagent.

Applicant has disclosed his invention in both generic and specific terms. Variations will occur to those of skill in the art, and examples and specific embodiments are not intended to be limiting, unless so indicated in the specification. Variations will occur to those of ordinary skill in the art without the exercise of inventive faculty. In particular, concentration levels, administration protocols, recombinant practices and varieties, and the like, will occur to those of skill in the art, and remain within the scope of invention, save as delimited by the claims set forth below.

What is claimed is:

1. A monoclonal antibody expressed by the hybridoma deposit accessible under Access No. ATCC HB12144.

2. A composition, comprising as an active agent the monoclonal antibody of claim 1, in a pharmaceutically acceptable carrier.

3. The composition of claim 2, wherein said composition comprises a concentration of monoclonal antibodies sufficient such that one dose of said composition effectively binds 100 percent of all sperm cells present in an ejaculate.

4. The composition of claim 3, wherein said monoclonal antibodies are present on the surface of liposomes.

5. The spermicide of claim 4, wherein said liposomes are non-phospholipid positively charged liposomes.

* * * * *

UNITED STATES PATENT AND TRADEMARK OFFICE
CERTIFICATE OF CORRECTION

PATENT NO. : 5,830,472
DATED : November 3, 1998
INVENTOR(S) : John C. Herr et al.

It is certified that error appears in the above-identified patent and that said Letters Patent is hereby corrected as shown below:

Column 1,
Line 6, the following paragraph is inserted:

U.S. Government Rights

This invention was made with United States Government support under Grant Nos. DK07642, HD07382, HD08002 and HD U54 29099, awarded by the National Institutes of Health. The United States Government has certain rights in the invention.

Signed and Sealed this

Twentieth Day of November, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 368 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

| | | | | | | |
|---|---|---|---|---|---|---|
| GACATTGTGC | TGACCCAATC | TCCAGCTTCT | CCCTGCCTGT | CAGTCTTGGA | GATCCAGCCT | 60 |
| CCATCTCTTG | CAGATCTAGT | CAGAGTCTTG | TACGCAGAAA | TAGAGACACC | TATTTACATT | 120 |
| GGTTCCTGCA | GAAGCCAGGC | CAGTCTCCAG | AGCTCCTGAT | CTACAGAGTT | CCAACCGAT | 180 |
| TTTCTGGGGT | CCCAGACAGG | TTCAGTGGCA | GTGGATCAGG | GACAGATTTC | ACACTCAAGA | 240 |
| TCAGCAGAGT | GGAGGCTGAG | GATCTGGGAG | TTTATTTCTG | TTCTCAAAGT | ACACATGTTC | 300 |
| CATTCACGTT | CGGCTCGGGG | ACAAAGTTGG | AAATAAAACG | GGCTGATGCT | GCACCAACTG | 360 |
| TATCCATC | | | | | | 368 |

(2) INFORMATION FOR SEQ ID NO:2:

(i) SEQUENCE CHARACTERISTICS:
(A) LENGTH: 466 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| GGGAATTCAT | GGAATGGAGC | TGGTTTTCCT | CTTCTTGGTA | GCAACAGCCT | CAGGTGTCCA | 60 |
| CTCCCAGGTC | CAATTGCAGC | AACCTGGTCT | GAACCGGTGA | GGCCTGGAGC | TTCAGTGAAG | 120 |
| GTGTCCTGCA | GGGCTTCTGG | CTACAAATTC | ACCACCTACT | GGATGCACTG | GGTGAGGCAG | 180 |
| AGGCCTGGAC | AAGGCCCTGA | GTGGATTGGA | GATATTTATC | CTGGTAGTGG | TGATTCTAAC | 240 |
| TACGATGTGA | AGTTCAAGAA | CAAGGCCACA | CTGACTGTAG | ACACATCCTC | CAGCACAGTT | 300 |
| TACATACAAC | TCAGCAGCCT | GACATCTGAG | GACTCCGCGG | TCTATTACTG | TGCAAGAAGG | 360 |
| GACTATGGTT | GCCCTTTTGT | TTACTGGGGC | CAAGGGACTC | TGGTCACTGT | CTCTGCAGCC | 420 |
| AAAACGACAC | CCCCATCCGT | TTATCCCCTG | GCCCCTAGAA | CTTGGG | | 466 |

(2) INFORMATION FOR SEQ ID NO:3:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:3:

| | | | |
|---|---|---|---|
| ACTAGTCGAC | ATGAGAGTGC | TGATTCTTTT | GTG | 33 |

(2) INFORMATION FOR SEQ ID NO:4:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:4:

```
CCCAAGCTTC  CAGGGRCCAR  KGGATARACG  RTGG                                              34
```

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "SYNTHETIC DNA"

( x i ) SEQUENCE DESCRIPTION: SEQ ID NO:5:

```
CCCCCCGGGG  ACATTGTGCT  GACCCAATCT  CCAGCTTCT                                         39
```

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "SYNTHETIC DNA"

( x i ) SEQUENCE DESCRIPTION: SEQ ID NO:6:

```
CCCCCCGGGG  ATGGATACAG  TTGGTGCAGC  ATCAGCCCG                                         39
```

( 2 ) INFORMATION FOR SEQ ID NO:7:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "SYNTHETIC DNA"

( x i ) SEQUENCE DESCRIPTION: SEQ ID NO:7:

```
CCANNNNNTG  G                                                                         11
```